(12) United States Patent
Haumann

(10) Patent No.: US 6,231,530 B1
(45) Date of Patent: May 15, 2001

(54) APPARATUS FOR IDENTIFYING THE POSITION OF THE FOCUS OF A SHOCK WAVE SOURCE

(75) Inventor: Hans-Juergen Haumann, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/315,481

(22) Filed: May 20, 1999

(30) Foreign Application Priority Data

May 20, 1998 (DE) ............................................. 198 22 793

(51) Int. Cl.[7] ................................................. A61B 17/22
(52) U.S. Cl. ................................................................. 601/4
(58) Field of Search ............................. 601/3.4; 600/439; 378/205, 162

(56) References Cited

U.S. PATENT DOCUMENTS

| | | | |
|---|---|---|---|
| 5,070,861 | * 12/1991 | Einars et al. | 601/4 |
| 5,488,951 | 2/1996 | Bauer et al. | |
| 5,658,239 | * 8/1997 | Delmenico | 601/4 |
| 5,666,954 | * 9/1997 | Chapelon et al. | 600/439 |
| 5,921,930 | * 7/1999 | Uberle | 600/439 |

FOREIGN PATENT DOCUMENTS 40 03 350    4/1991   (DE) .

* cited by examiner

*Primary Examiner*—Brian L. Casler
(74) *Attorney, Agent, or Firm*—Schiff Hardin & Waite

(57) ABSTRACT

An apparatus for identifying the position of the focus of a shock wave source which generates focused acoustic shock waves has a carrier that is connected directly to the shock wave source at a fixed location. The carrier is moveable relative to said shock wave source housing and carries a reference element which can be moved to a deployed position which identifies the position of the focus of the shock wave source and which can then be moved to a standby position out of the path of the shock waves.

6 Claims, 1 Drawing Sheet

APPARATUS FOR IDENTIFYING THE POSITION OF THE FOCUS OF A SHOCK WAVE SOURCE

BACKGROUND OF THE INVENTION

1. Field of the Invention

The present invention is directed to an apparatus for identifying the position of the focus of a shock wave source, the shock wave source generating focused acoustic shock waves.

2. Description of the Prior Art

An apparatus for identifying the position of the Focus of a shock wave source is disclosed German PS 40 03 350 for a therapy unit for treating patients with extracorporeally generated, focused shock waves, and serves the purpose of adjusting an x-ray apparatus relative to the therapy unit in order, for example, to be able to prepare diagnostic x-ray exposures of the treatment area of the patient during the treatment of a patient with focused shock waves. The apparatus has a conically fashioned carrier with a metal ball at the tip thereof that, when the carrier is put in place on the shock wave source, indicates the position of the therapy focus.

This known apparatus, however, has proven disadvantageous because the carrier that must be put in place on the shock wave source given every adjustment, or every check of the position of the focus of the shock wave source, is complicated to handle. There is thus the risk that the carrier, which cannot remain on the shock wave source during a treatment of a patient with the therapy unit, will be mislaid and may no longer be available when needed.

European Application 0 606 548 discloses an extracorporeal therapy apparatus having an electro-acoustic transducer for generating shock waves. A sound scanner is provided with a graticule that can be introduced into the focus of the transducer by a pivotable clip is arranged within the housing of the transducer. The clip with the graticule, however, is not arranged directly at the housing of the transducer nor is the clip so simple to handle so that it can be pivoted out of the path of the shock waves by an immediate and direct access by an operator. On the contrary, technical auxiliaries are required for this purpose.

SUMMARY OF THE INVENTION

It is an object of the present invention to provide an apparatus of the species initially described wherein the manipulation of the device for identifying the position of the focus of a shock wave source is simplified.

This object is inventively achieved in an apparatus of identifying the position of the focus of the shock wave source for generating focused acoustic shock waves a pivotable carrier that is rigidly connected directly to the shock wave source, the carrier support a reference element that identifies the position of the focus of the shock wave source when in its deployed condition. Due to the direct, permanent application of the carrier to the shock wave source, the apparatus is always advantageously at hand as needed, i.e. for checking the position of the focus of the shock wave source or for adjusting an adjustable x-ray apparatus relative to the shock wave source. Moreover, the manipulation of the apparatus is significantly simplified since the carrier for the reference element can be simply pivoted out (deployed) and—after being used—pivoted back by being directly grasped by an operator and without having to employ technical auxiliaries. Further, the permanent attachment of the apparatus to the shock wave source has the advantage that it cannot be lost.

For example, the pivotable carrier can be a clip or bow on which a metal ball is arranged as an x-ray-positive reference element for identifying the position of the focus of the shock wave source. The shock wave source in the case of the present invention is a shock wave source that has a housing in which or at which the components are arranged which are required for generating focused acoustic waves, for example an electromagnetic pressure pulse source, a positive lens and the coupling membrane closing a space filled with an acoustic propagation medium fluid-tight. The focus-identifying apparatus is preferably connected to the housing of the shock wave source at a fixed location (but still allowing pivoting of the carrier).

In one version of the invention the carrier of the apparatus can be fixed in a defined position. For example, the fixing can ensue by engagement of the part of the carrier with the housing or clamping of the carrier. The position of the focus of the shock wave source thus always can be advantageously dependably identified unmistakably and without being sensitive to unforseen impacts.

DESCRIPTION OF THE PREFERRED EMBODIMENTS

Figure 1:
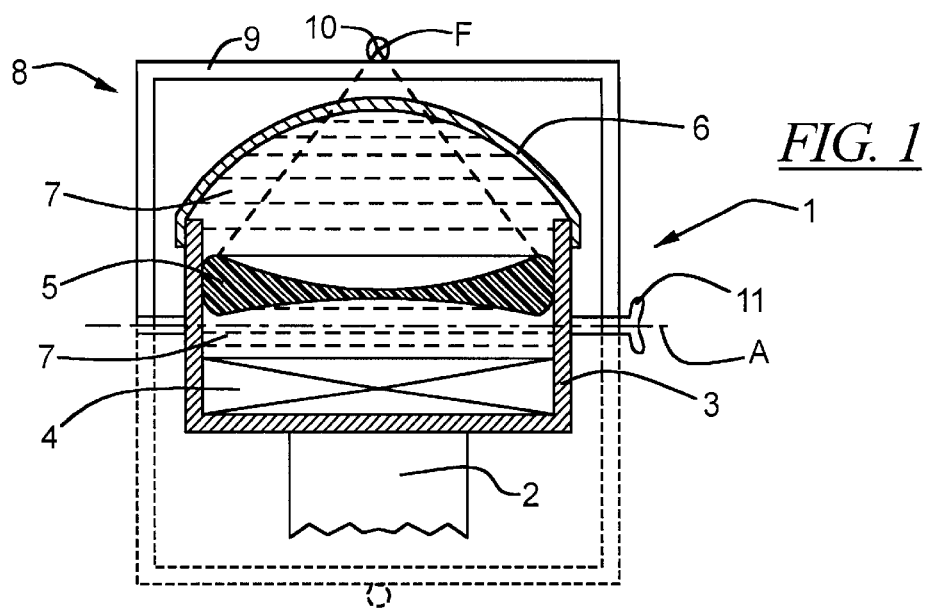
FIG. 1 shows a sectional view of a shock wave source, with a first embodiment of an apparatus in accordance with the invention for identifying the position of the focus of the shock wave source.

In a simplified, partially sectional view, FIG. 1 shows a shock wave source 1 for treating patients with extracorporeally generated, focused shock waves. The shock wave source 1 is arranged with a holder 2 at a therapy unit (not shown in FIG. 1) that can be stationary or portable.

In the exemplary embodiment, the shock wave source 1 has a housing 3 in which a pressure pulse source 4 (not shown in detail) and an acoustic positive lens 5 are arranged. At the patient side, the housing 3 is closed fluid-tight with a flexible coupling membrane 6. The space between the pressure pulse source 4 and the positive lens 5 as well as the space between the positive lens 5 and the coupling membrane 6 are filled with an acoustic propagation medium 7, which is water in the present case. The therapy unit (not shown) contains all units necessary for the operation of the shock wave source in a way that is known and thus not shown.

For example, the pressure pulse 4 can be an electromagnetic pressure pulse source which is disclosed in terms of its structure and function in European Applications 0 188 750 and 0 301 630. The high-voltage pulse generator that is required for the operation of the pressure pulse source 4 and is not explicitly shown in FIG. 1 is a component of the therapy unit to which the pressure pulse source 4 is connected via corresponding lines (not shown).

In the exemplary embodiment, the positive lens 5 is fashioned as a bi-concavely shaped solid lens that is formed of a material, for example polystyrol, in which the velocity of sound is higher than in the water provided as the acoustic propagation medium 7.

During operation of the shock wave source 1, pressure pulses emanate from the pressure pulse source 4, and the positive lens 5 focuses these pressure pulses onto a focus F, as indicated with broken lines in FIG. 1.

For identifying the position of the focus F of the shock wave source 1, an apparatus 8 is arranged directly at a fixedly location at the housing 3 of the shock wave source 1. The apparatus 8 has a pivotable carrier for a reference element. In the exemplary embodiment of FIG. 1, the carrier is a pivotable clip 9 at which a steel ball 10 is arranged as the reference element for identifying the position of the focus F of the shock wave source 1.

Figure 2:
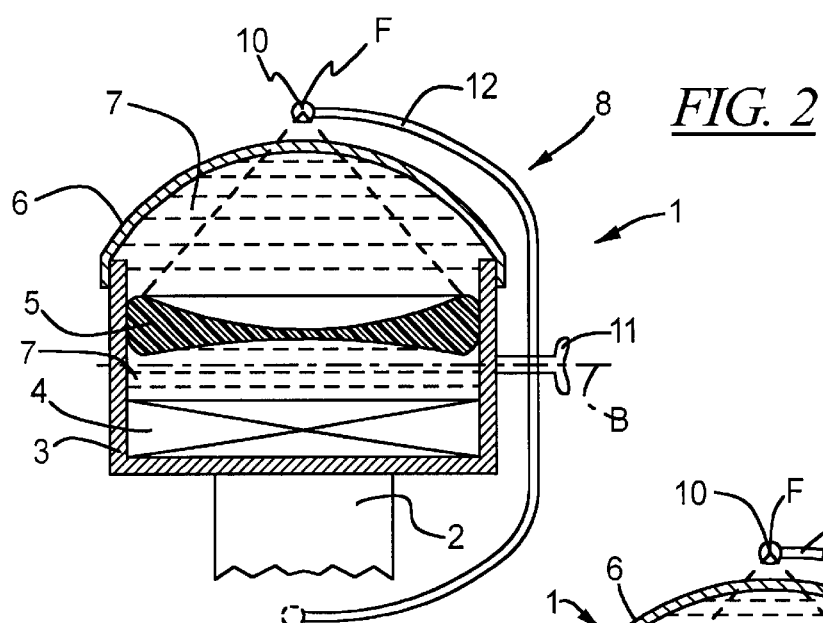
FIG. 2 shows a sectional view of a shock wave source, with a second embodiment of an apparatus in accordance with the invention for identifying the position of the focus of the shock wave source.
Figure 3:
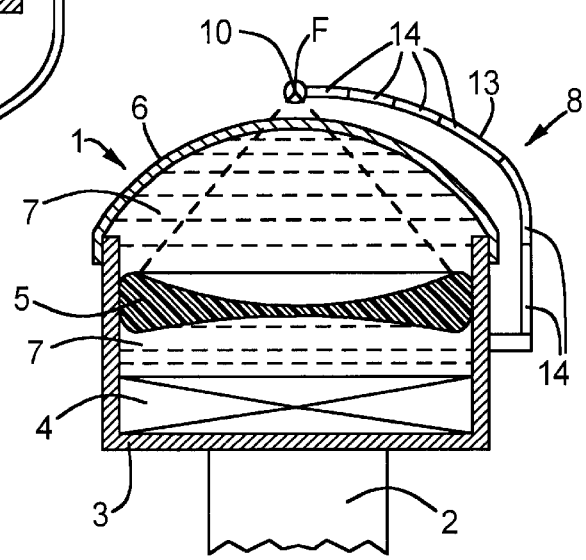
FIG. 3 shows a sectional view of a shock wave source, with a third embodiment of an apparatus in accordance with the invention for identifying the position of the focus of the shock wave source.

The immediate, fixed arrangement of such an apparatus 8 at the shock wave source 1 is especially advantageous when the therapy unit provided with the shock wave source 1 is provided, for example for treating a patient with focused shock waves together with an attachable, diagnostic x-ray apparatus that is not shown in FIGS. 1 through 3. In order to make such a treatment as convenient as possible, for example for an attending physician, the therapy unit and the diagnostic x-ray apparatus, for example a portable C-arm x-ray apparatus, must be aligned relative to one another such that the position of the focus F of the shock wave source 1 and the position of the isocenter of the C-arm of the x-ray apparatus are substantially identical. In this way, the course of the treatment of a patient with focused shock waves can be tracked without renewed alignment of the therapy unit and of the x-ray apparatus relative to one another on the basis of diagnostic x-ray exposures from different directions or, perspectives of the treatment area by adjusting the isocenter of the C-arm, or the results of the treatment can be visually displayed.

The inventive apparatus 8 thereby facilitates the alignment of the therapy unit or of the shock wave source 1 relative to the x-ray apparatus in that the position of the focus F of the shock wave source 1 is identified by the steel ball 10 by pivoting the clip 9 out into a defined position. For the purpose of alignment or for the purpose of checking the position of the focus F in the exemplary embodiment shown in FIG. 1, the clip 9 is arranged to be pivotable around an axis A at both sides at the housing 3 of the shock wave source 1. In its swivelled-out condition, the clip 9 can be fixed in a defined position with a schematically indicated locking screw 11, so that the clip cannot be inadvertently displaced by an impact which would cause the position of the focus F to be incorrectly indicated by the steel ball 10.

The fixing thereby need not necessarily ensue with a locking screw 11 but can also be effected by some other suitable means, for example by engagement of the clip 9 in a detent which sets the defined position as well.

When the alignment or the positional check of the focus F of the shock wave source 1 has ensued, the clip 9 can be pivoted into a standby position indicated with broken lines in FIG. 1, so that it does not have a disturbing influence on the treatment of the patient.

The immediate and fixed attachment of the clip 9 to the housing 3 of the shock wave source 1 proves advantageous because the clip 9 with the steel ball 10 is always at hand for checking the position of the focus F of the shock wave source 1, i.e. it is "captive" to the shock wave source 1 and can be manipulated very simply and without technical auxiliaries. Further, the apparatus 8 is also suitable for retrofitting shock wave sources that already exist.

FIG. 2 shows a further embodiment of an inventive apparatus 6 at the shock wave source 1 of FIG. 1. The apparatus 8 in FIG. 2 has a clip 12 that is adapted to the shape of the shock wave source 1 and is rigidly connected to the housing 3 of the shock wave source 1 at only one location. The clip 12 is again provided with a steel ball 10 as a reference element for identifying the position of the focus F of the shock wave source 1 and is pivotable around an axis B. The standby position of the clip 12 is entered with broken lines in FIG. 2.

FIG. 3 shows a third embodiment of the inventive apparatus 8 at the shock wave source 1 of FIG. 1. The apparatus 8 of FIG. 3 has a telescoping clip 13 that is constructed of individual elements 14 that engage inside one another. The elements 14 are pulled apart when the telescoping clip 13 is pivoted out. The elements 14 largely disappear inside one another when the telescoping clip 13 is pivoted in. The pivoted-in condition of the telescoping clip 13 corresponds to its standby position during the treatment of a patient. A steel ball 10 is again arranged at the end of the telescoping clip 13, this steel ball 10 identifying the position of the focus F of the shock wave source 1 in the pivoted-out condition of the telescoping clip 13.

Thus the inventive apparatus 8 can be realized in different ways and the embodiments of FIGS. 1 through 3 are to be understood only as examples.

The inventive apparatus was described above with reference to the example of a shock wave source 1 having an electromagnetic pressure pulse source an a positive lens. The use of the inventive apparatus, however, is not limited to shock wave sources of the type having an electromagnetic pressure pulse source and a positive lens. The shock wave source 1 can alternatively contain a piezoelectric pressure pulse source instead of an electromagnetic pressure pulse source. There is also the possibility of providing other sources of acoustic waves, for example an ultrasound source, instead of a pressure pulse source.

Further, the structure of the shock wave source can deviate from the structure of the shock wave source of the present examples. For example, the shock wave source can be provided with an ultrasound locating means or with an opening for the introduction of an ultrasound locating means.

Although modifications and changes may be suggested by those skilled in the art, it is the intention of the inventor to embody within the patent warranted hereon all changes and modifications as reasonably and properly come within the scope of his contribution to the art.

I claim as my invention:

1. For use with a shock wave source which has a housing and which generates shock waves converging at a focus at a focus position, an apparatus for identifying the position of said focus comprising:

a carrier having at least one end which is adapted for attachment at a fixed location to said housing; and a reference element disposed on said carrier, said carrier being movable relative to said housing to move said reference element to a position coinciding with the position of said focus and to move said reference element out of a path of said shock waves.

2. An apparatus as claimed in claim 1 further comprising means adapted for fixing said carrier element at a defined position relative to said housing to cause said reference element to assume said position coinciding with the position of said focus.

3. An apparatus as claimed in claim 1 wherein said carrier is adapted for pivotable attachment to said housing.

4. Apparatus as claimed in claim 1 wherein said carrier comprises a substantially rectangular clip having first and second ends adapted for pivotable attachment to said housing.

5. An apparatus as claimed in claim 1 wherein said carrier comprises a curved bow having a first end adapted for pivotable attachment to said housing, and a second end at which said reference element is disposed.

6. An apparatus as claimed in claim 1 wherein said carrier comprises a curved, bowed telescoping carrier having a first end adapted for rigid attachment to said housing and a second end at which said reference element is disposed.

* * * * *